United States Patent
Tekula

(10) Patent No.: US 11,058,107 B2
(45) Date of Patent: Jul. 13, 2021

(54) SPECIMEN CONTAINER FOR BIOLOGICAL MATERIALS

(71) Applicant: Francesca Dagny Tekula, McCordsville, IN (US)

(72) Inventor: Francesca Dagny Tekula, McCordsville, IN (US)

( * ) Notice: Subject to any disclaimer, the term of this patent is extended or adjusted under 35 U.S.C. 154(b) by 410 days.

(21) Appl. No.: 16/057,000

(22) Filed: Aug. 7, 2018

(65) Prior Publication Data

US 2018/0338489 A1 Nov. 29, 2018

Related U.S. Application Data

(63) Continuation of application No. 15/463,771, filed on Mar. 20, 2017, now abandoned, which is a
(Continued)

(51) Int. Cl.
*A01N 1/02* (2006.01)
*A61B 10/00* (2006.01)
(Continued)

(52) U.S. Cl.
CPC ......... *A01N 1/0263* (2013.01); *A01N 1/0273* (2013.01); *A61B 10/0096* (2013.01);
(Continued)

(58) Field of Classification Search
CPC . A01N 1/0263; A01N 1/0273; B01F 13/0023; B01L 3/561; B01L 3/563;
(Continued)

(56) References Cited

U.S. PATENT DOCUMENTS 8,343,426 B2 1/2013 Song
2003/0083621 A1* 5/2003 Shaw ................ A61M 25/0606
604/164.07

(Continued)

FOREIGN PATENT DOCUMENTS

WO WO 2012/019103 A2 2/2012

*Primary Examiner* — Benjamin R Whatley
*Assistant Examiner* — Jacqueline Brazin
(74) *Attorney, Agent, or Firm* — Frost Brown Todd LLC

(57) ABSTRACT

A specimen container that includes a first cylindrical housing section having a first threaded end, a second threaded end, and a body section formed therebetween, wherein a fill line is placed at a predetermined location on the body section; a threaded winged section that is adapted to be attached to the second threaded end of the first cylindrical housing section, wherein the threaded winged section includes two gripping wings formed on opposite sides of the threaded winged section; a second cylindrical housing section having a first threaded end, a second threaded end, and a body section formed therebetween, wherein two gripping wings are formed on opposite sides of the second cylindrical housing section and are integral therewith; a threaded connector ring that is adapted to connect the first cylindrical housing section to the second cylindrical housing section; and at least one syringe plunger adapted for insertion into the first cylindrical housing section or the second cylindrical housing section.

18 Claims, 4 Drawing Sheets

Related U.S. Application Data continuation-in-part of application No. 14/703,283, filed on May 4, 2015, now abandoned.

(60) Provisional application No. 61/987,577, filed on May 2, 2014.

(51) Int. Cl.
  *B01F 13/00* (2006.01)
  *B01L 3/00* (2006.01)

(52) U.S. Cl.
  CPC .......... *B01F 13/0023* (2013.01); *B01L 3/502* (2013.01); *B01L 3/561* (2013.01); *B01L 3/563* (2013.01); *B01L 3/565* (2013.01); *B01L 2200/025* (2013.01); *B01L 2200/026* (2013.01); *B01L 2200/028* (2013.01); *B01L 2200/0689* (2013.01); *B01L 2200/087* (2013.01); *B01L 2200/18* (2013.01); *B01L 2300/028* (2013.01); *B01L 2300/042* (2013.01); *B01L 2300/087* (2013.01); *B01L 2300/0832* (2013.01); *B01L 2400/0478* (2013.01)

(58) Field of Classification Search
  CPC .... B01L 3/565; B01L 3/502; B01L 2200/025; B01L 2200/028; B01L 2200/18; B01L 2300/028; B01L 2300/087; B01L 2300/0832; B01L 2300/042; B01L 2400/0478; B01L 2200/026; B01L 2200/0689; B01L 2200/087; A61B 10/0096
  USPC .......................................................... 422/545
  See application file for complete search history.

(56) References Cited

U.S. PATENT DOCUMENTS

| | | | |
|---|---|---|---|
| 2012/0058027 A1* | 3/2012 | Song ..................... | B01L 3/5021 422/533 |
| 2013/0158515 A1* | 6/2013 | Austen, Jr. ........... | C12N 5/0653 604/522 |
| 2014/0123776 A1* | 5/2014 | Singer ................... | B01L 3/0217 73/864.01 |
| 2015/0314284 A1 | 11/2015 | Tekula | |
| 2017/0188572 A1 | 7/2017 | Tekula | |

* cited by examiner

SPECIMEN CONTAINER FOR BIOLOGICAL MATERIALS

CROSS-REFERENCE TO RELATED APPLICATIONS

This patent application is a continuation of U.S. patent application Ser. No. 15/463,771 filed on Mar. 20, 2017 and entitled "Specimen Container for Biological Materials", which was a continuation-in-part of U.S. patent application Ser. No. 14/703,283, filed on May 4, 2015 and entitled Specimen Container for Biological Materials, which claimed the benefit of U.S. Provisional Patent Application Ser. No. 61/987,577 filed on May 2, 2014 and entitled "Specimen Container for Biological Materials," the disclosures of which are hereby incorporated by reference herein in their entirety and made part of the present U.S. utility patent application for all purposes.

BACKGROUND OF THE INVENTION

The described invention relates in general to containers for use with biological specimens and samples, and more specifically to a container for use with bone samples harvested from living patients. Proper collection and preparation of bone marrow is critical to the study of a variety of hematologic and neoplastic disorders. Dry bone core samples will desiccate and be useless for any study, including slides/morphology. Thus, there is an ongoing need for a container that may be used to effectively store and transport bone samples or other biological materials without damaging or otherwise rendering useless the sample.

SUMMARY OF THE INVENTION

The following provides a summary of certain exemplary embodiments of the present invention. This summary is not an extensive overview and is not intended to identify key or critical aspects or elements of the present invention or to delineate its scope. This invention provides various containers for use with biological specimens and other samples, and more specifically to a container for use with bone samples harvested from living patients which can be used with cryopreservative and kept at as low as negative 80 degrees for short or long term storage. These containers can then be used with additional parts to enable the bone samples to be mixed with other additives and then delivered to another target area.

Exemplary embodiments of this invention provide containers for storing and transporting biological specimens and samples, and more specifically to containers for storing, transporting, and preserving bone samples and/or other cell or tissue specimens which allows for collection in a sterile fashion as well as addition of cryopreservative in sterile fashion either immediately (in a first container) or in a delayed fashion (in a second container). Included is at least one smooth cylindrical housing, wherein the at least one smooth cylindrical housing is open on both ends and threaded thereon, wherein one end has thicker threading at its base thread; and at least one cap with ring for completely sealing the open ends of the at least one cylindrical housing. If only one cap is used, a plunger stopper with two valves with depressed threaded area and cap is used. Both valves can be removed and immediately sealed, if desired. One valve is typically longer than the other and includes a luer connection or similar connection to facilitate filling, and the other valve is shorter with an inline filter to serve as a relief valve. The first and second containers also have fill lines marked thereon. In the first container, the fill mark can be on either end. In the second container, the file line is placed on the end with the thicker bottom thread, which is the end which is designed to accept the plunger stopper.

After cryopreservation of a sample or specimen, the first and second containers may be used with separately packed mesh screen to simply rinse and decant specimen before use. Alternatively, separately packaged threaded cuff, ring with wings, and two plungers with plunger stoppers can be used with first container to permit gently mixing of the contents thereof with demineralized bone matrix (DBM), bone marrow aspirate (BMA) or other materials and compositions, per the choice of the surgeon using the container. Separately packaged threaded cuff, ring with wings, one plunger with plunger stopper, and one plunger with threaded end can be used with the second container to permit gently mixing of the contents thereof.

The first and second containers, including cylindrical housings, caps with ring seals, plunger stoppers with valves and threaded depressions, may be manufactured using cryo-compatible materials such as silicone and EVA that can be sterilized. The third container including threaded cuff, ring with wings, plunger with plunger stopper, threaded plunger, and mesh screen may be manufactured from any variety of suitable materials that can be sterilized. All three containers may be provided in at least 5 and 10 cc sizes. The threaded cuffs have ridges on the outside surfaces thereof, approximately 10 mm apart and perpendicular to the inner threads to allow for ease in use to lock into other threads and be disassembled. The caps include similar outer ridges and O-rings placed inside the caps.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention relates generally to a container for storing and transporting biological specimens and samples, and more specifically to a container for storing, transporting, and preserving bone samples (and/or other cell or tissue specimens) that includes at least one cylindrical housing, wherein the at least one cylindrical housing is open on one or both ends thereof; at least one cap for completely sealing the open ends of the at least one cylindrical housing; a syringe plunger adapted for insertion into the at least one cylindrical housing, wherein the syringe plunger is operative to move a biological specimen further into the at least one cylindrical housing when the syringe plunger is depressed; and optionally, a linking cuff, wherein the linking cuff is operative to join multiple cylindrical housings to one another and permit mixing of the contents thereof with demineralized bone matrix (DBM) or other materials and compositions, per the choice of the surgeon using the container.

Figure 1:
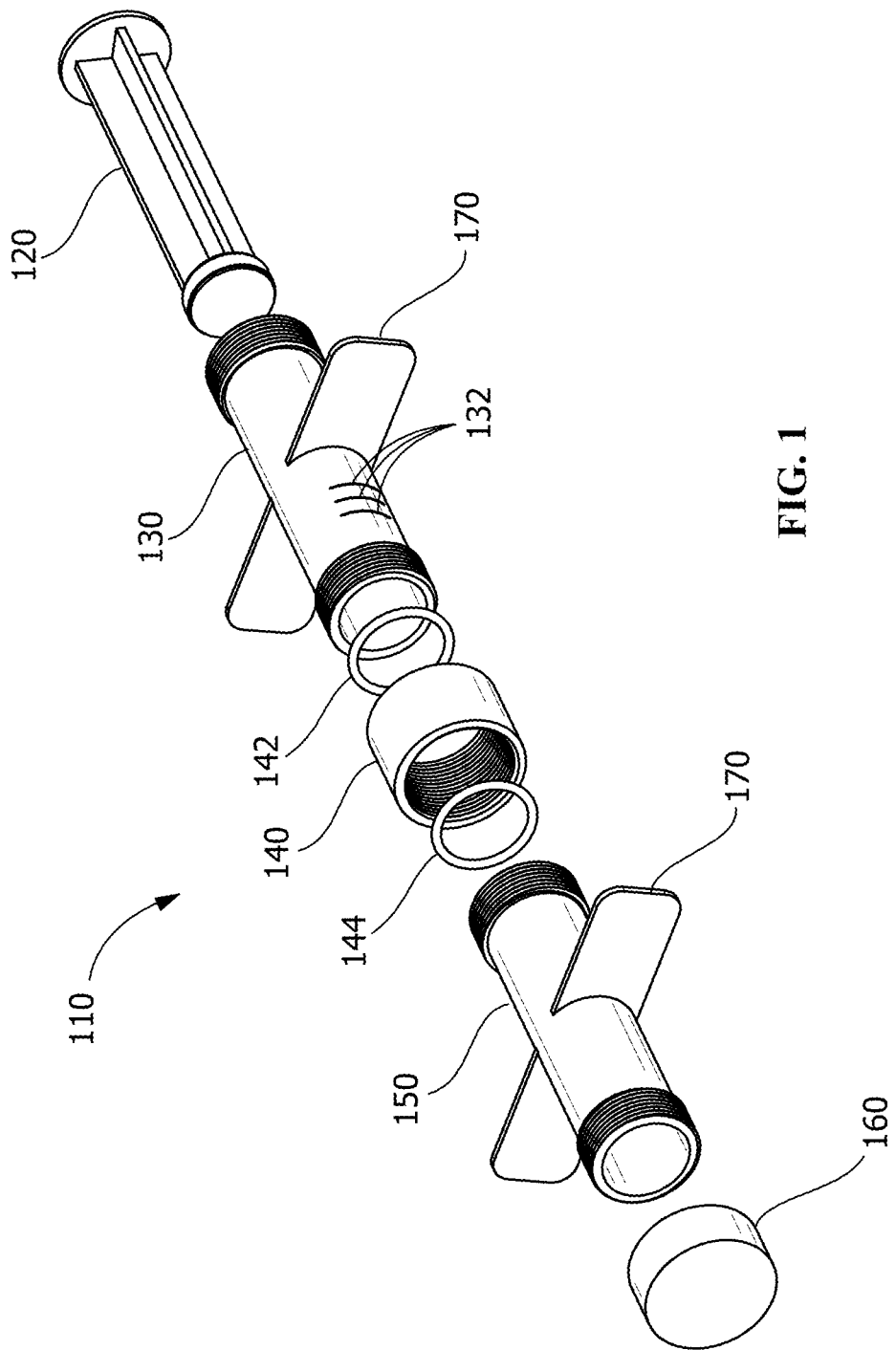
FIG. 1 is an exploded view of a first exemplary embodiment of the specimen container of the present invention.
Figure 2:
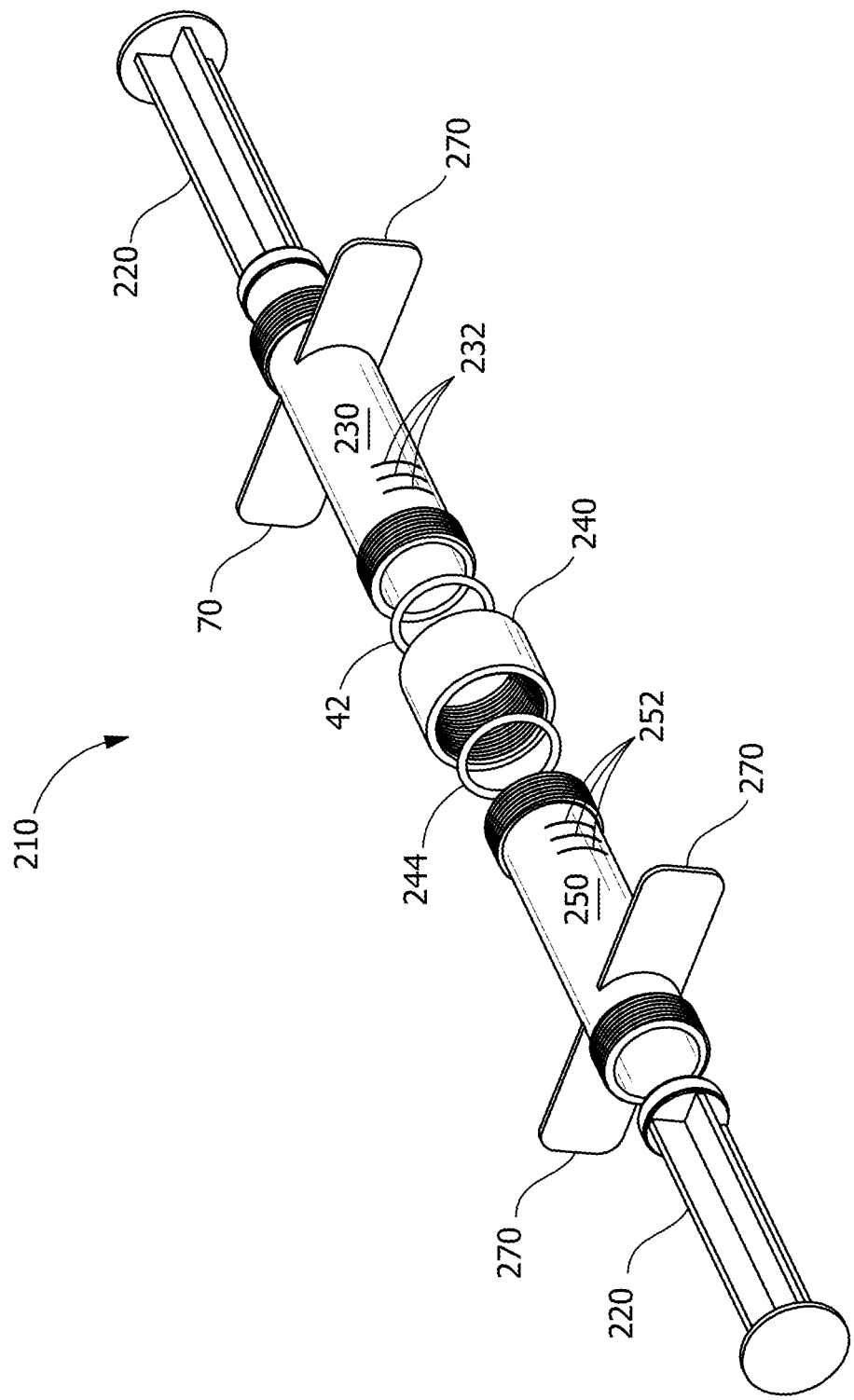
FIG. 2 is an exploded view of a second exemplary embodiment of the specimen container of the present invention.

FIG. 1 and FIG. 2 are exploded, perspective views of a specimen container in accordance with an exemplary embodiment of the present invention. In FIG. 1, container 110 includes plunger 120, first housing section 130, which is threaded on both ends thereof; threaded linking cuff 140; second housing section 150, which is also threaded on both ends thereof; and threaded cap 160. In FIG. 2, threaded cap 160 has been replaced with plunger 220. Housing sections 230 and 250 also include wing structures 270, which provide gripping surfaces that facilitate depression of plunger 220, when in use. In some embodiments, only one housing section is used and cap 160 is threaded onto the end of housing section 130 opposite the end into which plunger 120 is inserted. In other embodiments, two or more housing sections are joined together for mixing the contents thereof or for simply increasing the volume thereof. When multiple housing sections are used, threaded linking cuff 140/240 is used to attach the sections to one another. O-rings, gaskets, or other rubberized components may be included to enhance the sealing properties of container 110/210 and to more effectively join the components thereof to one another.

Each cylindrical housing, as well as the caps and cuffs, may be manufactured from any variety of materials that are suitable for storing and transporting biological materials and each housing may be graduated for providing the user with an indication of the amount of material stored in each container. The container may be provided in 5 and 10 cc sizes, although other dimensions and volumes are possible. The containers of the present invention are typically provided as sterile devices and various stabilizers and/or preservatives may be pre-loaded into the containers, if appropriate and/or desirable.

Proper collection of bone samples in a sterile manner and the sterile preparation thereof with cryo-preservative is important for its storage and repurposing and is important with regard to different orthopedic and neurosurgery procedures for patients and for additional study and use. Thus, in certain exemplary embodiments, this invention provides a container that may be effectively used to collect, store, transport, and deliver bone samples or other biological materials such as cell or tissue specimens without contaminating them or damaging them or otherwise rendering the samples useless.

In exemplary embodiments, there are multiple types of specimen containers usable for collection of a biological sample, addition of cryo-preservative to the sample, and storage and ultimately delivery of the sample. One exemplary specimen container includes one smooth cylindrical housing, wherein the housing is open on both ends thereof and wherein both ends are threaded; and two caps for sealing the open ends of the cylindrical housing with rings in a sterile manner. This specimen container is for use when a cryo-preservative can be added immediately at the time of acquiring a bone sample or other biological specimen. The second specimen container includes one smooth cylindrical housing, wherein the housing is open on both ends thereof and wherein both ends are threaded; and one cap for sealing the open end of the cylindrical housing with a ring in a sterile manner. The other end incudes a plunger stopper which fits in the end of the cylindrical housing; an attached fill and relief valve; and a threaded depression which can later be threaded into a plunger piece for use. The valves can be cut off and immediately sealed to preserve sterility of the contents of the container. Furthermore, the plunger stopper can seat within the cylindrical container such that when valves are removed, a sterile cap with ring for seal can be placed over the top of the cylindrical housing for sterile storage. Because cryopreservation is part of the purpose of cylindrical housing, the materials used to make the various parts of these devices include cryo-compatible materials such as, for example, silicone and EVA that can be sterilized.

Figure 3:
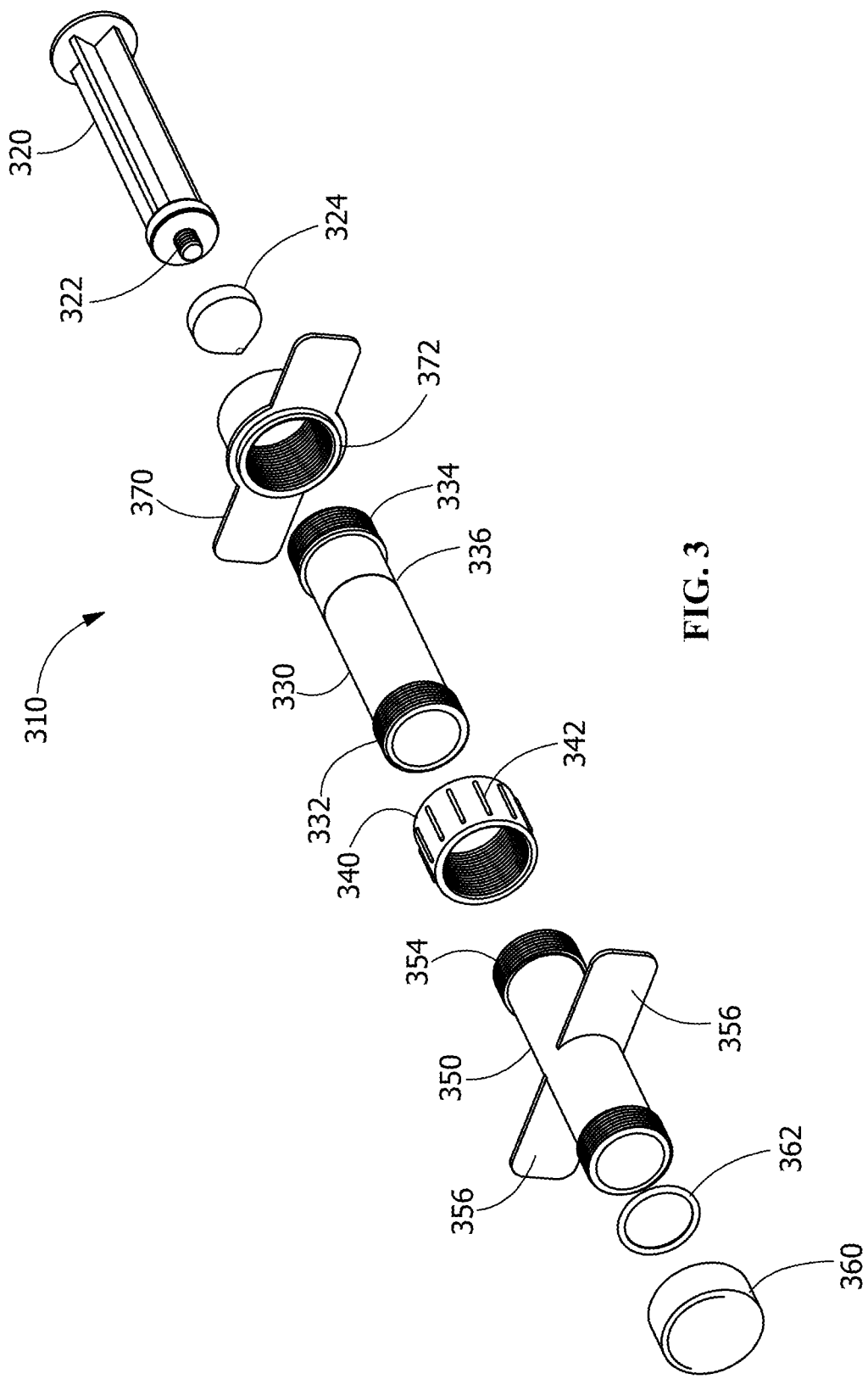
FIG. 3 is an exploded view of a third exemplary embodiment of the specimen container of the present invention.

FIG. 3 provides an exploded view of a third exemplary embodiment of the specimen container of the present invention. In this embodiment, container 310 includes plunger 320, which further includes threaded stem 322 to which optional stopper 324 may be attached using threaded depression 326. Stopper 324 typically includes two check-valves formed therein. First housing section 330 includes first threaded end 332 and second threaded end 334, to which detachable winged section 370 may be attached using internal threads 372. The terminal thread on second threaded end 334 is thicker in diameter than the adjacent threads. Fill line 336 is formed, etched, or painted onto the interior and/or exterior of first housing section 330. Threaded connector ring 340, which includes gripping ridges 342 formed on the exterior thereof is used to connect first housing section 330 to second housing section 350 at first threaded end 332 (of first housing section 330) and second threaded end 354 (of second housing section 350). Cap 360 and O-ring 362 are used to close and seal second housing portion 350 when cap 360 is screwed onto first threaded end 352. Integral gripping wings 356 are formed on either side of second housing section 350.

Figure 4:
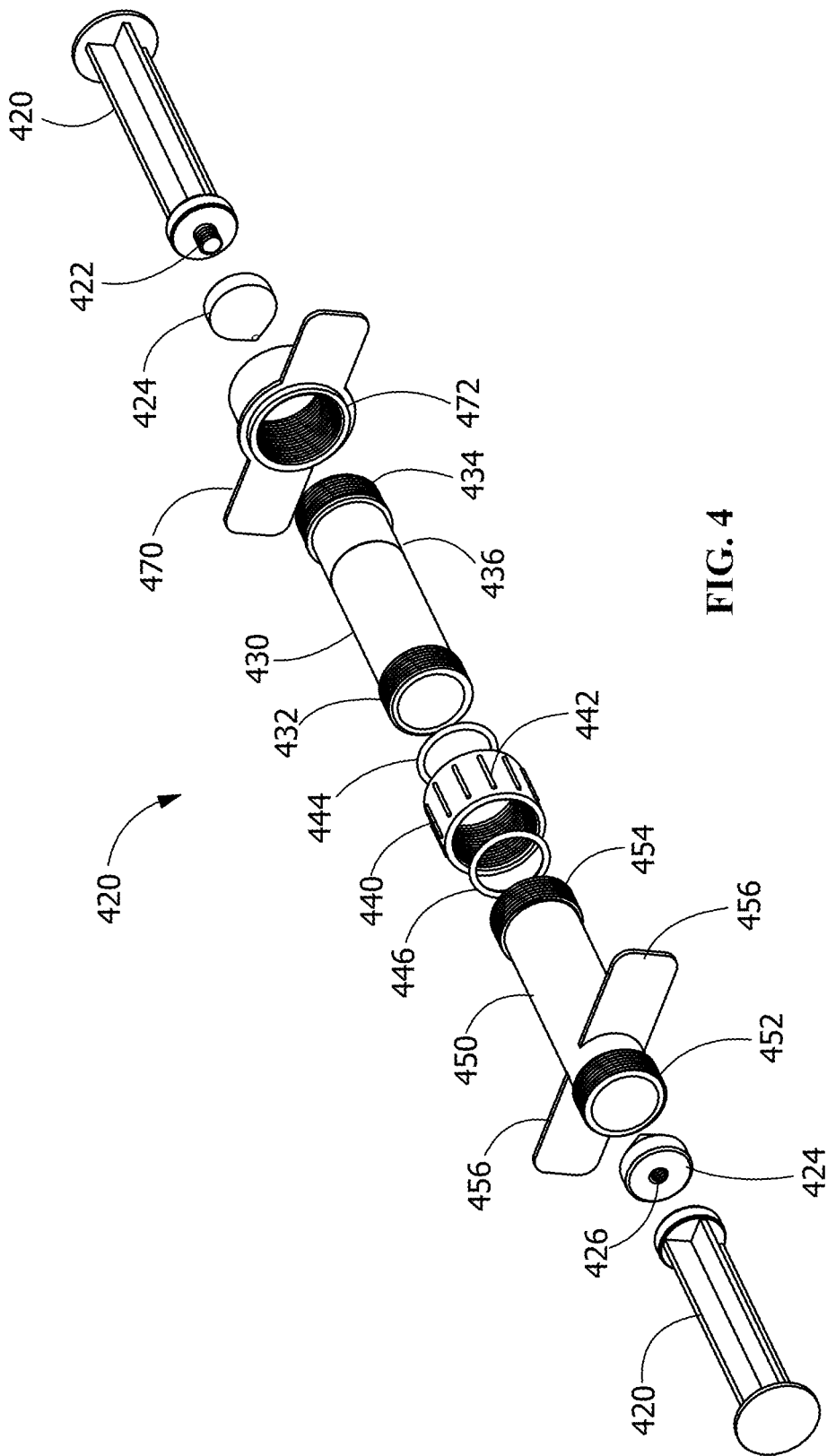
FIG. 4 is an exploded view of a fourth exemplary embodiment of the specimen container of the present invention.

FIG. 4 provides an exploded view of a fourth exemplary embodiment of the specimen container of the present invention. In this embodiment, container 410 includes plunger 420, which further includes threaded stem 422 to which optional stopper 424 may be attached using threaded depression 426. Stopper 424 typically includes two check-valves formed therein. First housing section 430 includes first threaded end 432 and second threaded end 434, to which detachable winged section 470 may be attached using internal threads 472. The terminal thread on second threaded end 434 is thicker in diameter than the adjacent threads. Fill line 436 is formed, etched, or painted onto the interior and/or exterior of first housing section 430. Threaded connector ring 440, which includes gripping ridges 442 formed on the exterior thereof is used to connect first housing section 430 to second housing section 450 at first threaded end 432 (of first housing section 430) and second threaded end 454 (of second housing section 450) and O-rings 444 and 446 provide additional sealing functionality. Integral gripping wings 456 are formed on either side of second housing section 450. A second plunger 420 includes a threaded stem (not visible in Figure) to which stopper 424 is attached using threaded depression 426. Stopper 424 typically includes two check-valves formed therein. A threaded cap (not shown in FIG. 4) may also be used to close second housing section 450 by tightening the threaded cap onto first threaded end 452.

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the general inventive concept.

What is claimed:

1. A specimen container for use with biological specimens, comprising:
   (a) a first cylindrical housing section having a first threaded end, a second threaded end, and a body section formed between the first threaded end and second threaded end, wherein a fill line is placed at a predetermined location on the body section;
   (b) a threaded winged section that is adapted to be attached to the second threaded end of the first cylindrical housing section, wherein the threaded winged section includes two gripping wings formed on opposite sides of the threaded winged section;
   (c) a second cylindrical housing section having a first threaded end, a second threaded end, and a body section formed between the first threaded end and second threaded end, wherein two gripping wings are formed on opposite sides of the second cylindrical housing section and are integral therewith;
   (d) a threaded connector ring that is adapted to connect the first cylindrical housing section to the second cylindrical housing section; and
   (e) at least one syringe plunger adapted for insertion into the first cylindrical housing section or the second cylindrical housing section, wherein the at least one syringe plunger is operative to move a biological specimen into the first cylindrical housing section or the second cylindrical housing section when the syringe plunger is depressed, and further wherein the at least one syringe plunger includes a threaded stem formed on one end thereof, and further wherein a stopper including two valves formed therein is mounted on the threaded stem.

2. The specimen container of claim 1, further comprising a threaded cap and O-ring for closing and sealing the second cylindrical housing section when mounted on the first threaded end thereof.

3. The specimen container of claim 1, further comprising two O-rings adapted to cooperate with the threaded connector wing for forming seals between the first and second cylindrical housing sections.

4. The specimen container of claim 1, wherein the first cylindrical body section is graduated.

5. The specimen container of claim 1, wherein the volume of the first cylindrical body section is 5 cc to 10 cc.

6. A specimen container for use with biological specimens, comprising:
   (a) a first cylindrical housing section having a first threaded end, a second threaded end, and a body section formed between the first threaded end and second threaded end, wherein a fill line is placed at a predetermined location on the body section;
   (b) a threaded winged section that is adapted to be attached to the second threaded end of the first cylindrical housing section, wherein the threaded winged section includes two gripping wings formed on opposite sides of the threaded winged section;
   (c) a second cylindrical housing section having a first threaded end, a second threaded end, and a body section formed between the first threaded end and second threaded end, wherein two gripping wings are formed on opposite sides of the second cylindrical housing section and are integral therewith;
   (d) a threaded connector ring that is adapted to connect the first cylindrical housing section to the second cylindrical housing section;
   (e) a first syringe plunger adapted for insertion into the first cylindrical housing section, the first syringe plunger including a threaded stem formed on one end thereof;
   (f) a stopper including two valves formed therein, wherein the stopper is mounted on the threaded stem; and
   (g) a second syringe plunger adapted for insertion into the second cylindrical housing section;
   wherein the first syringe plunger is operative to move a biological specimen into the first cylindrical housing section when the first syringe plunger is depressed and the second syringe plunger is operative to move a biological specimen into the second cylindrical housing section when the second syringe plunger is depressed.

7. The specimen container of claim 6, further comprising a threaded cap and O-ring for closing and sealing the second cylindrical housing section when mounted on the first threaded end thereof.

8. The specimen container of claim 6, further comprising two O-rings adapted to cooperate with the threaded connector wing for forming seals between the first and second cylindrical housing sections.

9. The specimen container of claim 6, wherein the first cylindrical body section is graduated.

10. The specimen container of claim 6 wherein the volume of the first cylindrical body section is 5 cc to 10 cc.

11. The specimen container of claim 6, wherein the second syringe plunger further includes a threaded stem formed on one end thereof, wherein a stopper is mounted on the threaded stem, and wherein the stopper includes two valves formed therein.

12. A specimen container for use with biological specimens, comprising:
   (a) a first cylindrical housing section having a first threaded end, a second threaded end, and a body section formed between the first threaded end and second threaded end, wherein a fill line is placed at a predetermined location on the body section;
   (b) a threaded winged section that is adapted to be attached to the second threaded end of the first cylindrical housing section, wherein the threaded winged section includes two gripping wings formed on opposite sides of the threaded winged section;
   (c) a second cylindrical housing section having a first threaded end, a second threaded end, and a body section formed between the first threaded end and second threaded end, wherein two gripping wings are formed on opposite sides of the second cylindrical housing section and are integral therewith;

(d) a threaded connector ring that is adapted to connect the first cylindrical housing section to the second cylindrical housing section;

(e) a first syringe plunger adapted for insertion into the first cylindrical housing section, wherein the first syringe plunger further includes a threaded stem formed on one end thereof, wherein a stopper is mounted on the threaded stem, and wherein the stopper includes two valves formed therein; and (f) a second syringe plunger adapted for insertion into the second cylindrical housing section, wherein the second syringe plunger further includes a threaded stem formed on one end thereof, wherein a stopper is mounted on the threaded stem, and wherein the stopper includes two valves formed therein;

wherein the first syringe plunger is operative to move a biological specimen into the first cylindrical housing section when the first syringe plunger is depressed and the second syringe plunger is operative to move a biological specimen into the second cylindrical housing section when the second syringe plunger is depressed.

13. The specimen container of claim 12, further comprising a threaded cap and O-ring for closing and sealing the second cylindrical housing section when mounted on the first threaded end thereof.

14. The specimen container of claim 12, further comprising two O-rings adapted to cooperate with the threaded connector wing for forming seals between the first and second cylindrical housing sections.

15. The specimen container of claim 12, wherein the first cylindrical body section is graduated.

16. The specimen container of claim 12, wherein the volume of the first cylindrical body section is 5 cc to 10 cc.

17. The specimen container of claim 1, further comprising:

(a) a threaded cap and O-ring for closing and sealing the second cylindrical housing section when mounted on the first threaded end thereof; and (b) two O-rings adapted to cooperate with the threaded connector wing for forming seals between the first and second cylindrical housing sections;

wherein the first cylindrical body section is graduated.

18. The specimen container of claim 6, further comprising:

(a) a threaded cap and O-ring for closing and sealing the second cylindrical housing section when mounted on the first threaded end thereof; and (b) two O-rings adapted to cooperate with the threaded connector wing for forming seals between the first and second cylindrical housing sections;

wherein the first cylindrical body section is graduated.

* * * * *